United States Patent [19]
Kajita et al.

[11] Patent Number: 5,376,498
[45] Date of Patent: Dec. 27, 1994

[54] NEGATIVE TYPE RADIATION-SENSITIVE RESIN COMPOSITION

[75] Inventors: Toru Kajita; Eiichi Kobayashi; Toshiyuki Ota; Takao Miura, all of Yokkaichi, Japan

[73] Assignee: Japan Synthetic Rubber Co., Ltd., Tokyo, Japan

[21] Appl. No.: 975,713

[22] Filed: Nov. 13, 1992

[30] Foreign Application Priority Data

Nov. 15, 1991 [JP] Japan ................... 3-326748

[51] Int. Cl.⁵ ............................................. G03C 1/52
[52] U.S. Cl. ...................................... 430/191; 430/270; 430/281; 430/325; 430/192
[58] Field of Search ................ 430/270, 325, 281, 191, 430/192; 522/31, 47

[56] References Cited

U.S. PATENT DOCUMENTS 4,929,536 5/1990 Spak et al. ........................... 430/325
4,931,381 6/1990 Spak et al. ........................... 430/325
5,217,840 6/1993 Spak et al. ........................... 430/325

FOREIGN PATENT DOCUMENTS 0361907 4/1990 European Pat. Off. .
0436174 7/1991 Germany .
2-120366 5/1990 Japan .
2-170165 6/1990 Japan .
WO8802878 4/1988 WIPO .

Primary Examiner—Marion E. McCamish
Assistant Examiner—Laura S. Weiner
Attorney, Agent, or Firm—Oblon, Spivak, McClelland, Maier, & Neustadt

[57] ABSTRACT

A negative type radiation-sensitive resin composition which comprises (A) an alkali-soluble resin, (B) a compound which generates an acid upon irradiation, and (C) an aromatic compound having, as functional groups, an —OR group and a —CH$_2$OX group, both directly bonded to the aromatic ring in which R represents a substituted methyl group, a substituted ethyl group, a silyl group, an alkoxycarbonyl group or an acyl group and in which X represents a hydrogen atom, an alkyl group having 1–5 carbon atoms or an R group which is as defined above, said aromatic compound being capable of cross-linking the alkali-soluble resin (A) in the presence of an acid, and optionally (D) a specific phenolic compound. The negative type radiation-sensitive resin composition is excellent in developability, pattern-formation, resolution and thermal durability.

27 Claims, No Drawings

NEGATIVE TYPE RADIATION-SENSITIVE RESIN COMPOSITION

This invention relates to a negative type radiation-sensitive resin composition, and more particularly, to a negative type radiation-sensitive resin composition suitable as a resist for fabricating a VLSI which is sensitive to radiation such as ultraviolet rays, far ultraviolet rays, X rays, electron beam, molecular beam, gamma rays, synchrotron radiation, proton beam or the like.

In the field of micro engineering, representative of which is fabrication of integrated circuit elements, a lithographic process enabling to produce critical dimensions of sub-half-micron is now being developed in order to obtain a higher packing density.

In recent years, it has been found that by applying a resist to a phase-shifting mask technology, the contrast of radiation intensity is increased, whereby a high resolvability is obtained.

However, when a positive type resist is applied to the above process, in the formation of isolated pattern, the intensity of radiation is reduced owing to shift of phase at the boundary of shifters used in the phase shift, and therefore, the portion to be primarily removed during development remains unremoved and causes troubles.

A negative type resist composition comprising an alkali-soluble resin, a compound which generates an acid upon irradiation, and a conventional cross-linking agent tends to undergo thermal cross-linking upon pre-baking in the formation of negative type resin layer on a wafer because the thermal stability of the cross-linking agent is insufficient, resulting in a lower resolution. In addition, when the negative type resist composition comprises a melamine-type cross-linking agent which is one of the conventional cross-linking agents, the yield of residual film thickness at the irradiated portion at which a pattern has been formed becomes low and swelling of a pattern during development tends to occur and formation of curved pattern tends to be caused.

An object of this invention is to provide a negative type radiation-sensitive resin composition.

Another object of this invention is to provide a negative type radiation-sensitive resin composition excellent in developability, pattern-formation, resolution and thermal durability.

A further object of this invention is to provide a negative type radiation-sensitive resin composition which has solved problems such as insufficient stability of cross-linking agent; reduction in yield of residual film thickness at the irradiated portion at which a pattern has been formed; swelling of pattern during development; formation of curved lines in pattern; and the like.

Other objects and advantages of this invention will become apparent from the following description.

According to this invention, there is provided a negative type radiation-sensitive resin composition, which comprises:

(A) an alkali-soluble resin [referred to hereinafter as the resin (A)], (B) a compound which generates an acid upon irradiation [referred to hereinafter as the acid-generating agent (B)], and (C) an aromatic compound having, as functional groups, an —OR group directly bonded to the aromatic ring in which R represents a substituted methyl group, a substituted ethyl group, a silyl group, an alkoxycarbonyl group or an acyl group, and a —CH$_2$OX group directly bonded to the aromatic ring in which X represents a hydrogen atom, an alkyl group having 1-5 carbon atoms or an R group which is as defined above [referred to hereinafter as the cross-linking agent (C)], said aromatic compound being capable of cross-linking the resin (A) in the presence of an acid.

This invention further provides another negative type radiation-sensitive resin composition which comprises the above-mentioned negative type radiation-sensitive resin composition and a phenolic compound represented by structural formula (1) [referred to hereinafter as the swelling-inhibiting agent (D)]:

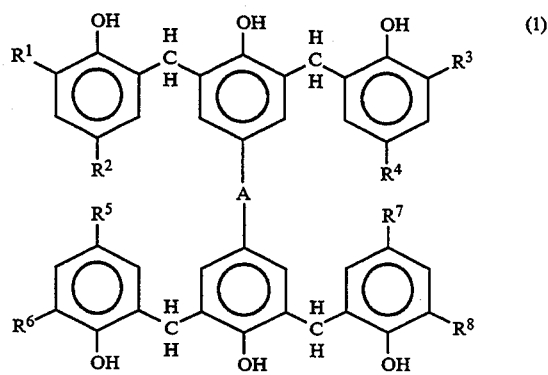

wherein each of $R^1$-$R^8$ represents a substituent selected from the group consisting of hydrogen atom, alkyl groups having 1-4 carbon atoms and alkoxy groups having 1-4 carbon atoms; A represents a single bond, —S—, —SO$_2$—,

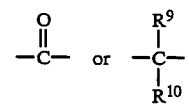

in which each of $R^9$ and $R^{10}$ represents a substituent selected from the group consisting of hydrogen atom, alkyl groups having 1-4 carbon atoms, phenyl group and hydroxyphenyl group, provided that when both $R^9$ and $R^{10}$ are alkyl groups they may be bonded to each other through a single bond.

The negative type radiation-sensitive resin composition of this invention is explained in detail below.

The cross-linking agent (C) used in this invention is an aromatic compound having, as functional groups, an —OR group and an —CH$_2$OX group, both being bonded directly to the aromatic ring, as mentioned above.

R of the —OR group is as defined above. The substituted methyl group in the definition of R includes, for example, methoxymethyl, methylthiomethyl, methoxyethoxymethyl, tetrahydropyranyl, tetrahydrofuryl, tetrahydrothiopyranyl, benzyloxymethyl, phenacyl, bromophenacyl, methoxyphenacyl, α-methylphenacyl, cyclopropylmethyl, cyclopentyl, cyclohexyl, benzyl, ortho-methylbenzyl, meta-methylbenzyl, para-methylbenzyl, triphenylmethyl, diphenylmethyl, bromobenzyl, chlorobenzyl, dichlorobenzyl, nitrobenzyl, methoxybenzyl, piperonyl, allyl and the like.

The substituted ethyl group in the definition of R includes, for example, 1-methoxyethyl, 1-ethoxyethyl, isopropyl, t-butyl, 1,1-dimethylpropyl and the like.

The silyl group in the definition of R includes, for example, trimethylsilyl, triethylsilyl, t-butyldimethylsilyl, isopropyldimethylsilyl, phenyldimethylsilyl and the like.

The alkoxycarbonyl group in the definition of R includes, for example, methoxycarbonyl, ethoxycarbonyl, t-butoxycarbonyl and the like.

The acyl group in the definition of R includes, for example, acetyl, propionyl, butyryl, heptanoyl, hexanoyl, valeryl, pivaloyl, isovaleryl, lauroyl, myristoyl, palmitoyl, stearoyl, acryloyl, propioloyl, methacryloyl, crotonoyl, oleoyl, furoyl, thenoyl, nicotinoyl, isonicotinoyl, p-toluenesulfonyl, mesyl and the like.

Of these R groups, the following groups are preferred: tetrahydropyranyl, tetrahydrofuryl, benzyl, o-methylbenzyl, m-methylbenzyl, p-methylbenzyl, triphenylmethyl, diphenylmethyl, nitrobenzyl, methoxybenzyl, piperonyl, allyl, 1-methoxyethyl, t-butyl, trimethylsilyl, methoxycarbonyl, ethoxycarbonyl, t-butoxycarbonyl, acetyl and p-toluenesulfonyl.

X of the $-CH_2OX$ group represents a hydrogen atom, an alkyl group having 1-5 carbon atoms or an R group which is as defined above.

The alkyl group having 1-5 carbon atoms in the definition of X may be of straight chain or branched chain, and includes, for example, methyl, ethyl, n-propyl, isopropyl, n-butyl, isobutyl, sec-butyl, t-butyl, n-pentyl and the like.

In order to facilitate the cross-linking of the functional $-CH_2OX$ group with resin (A) in the presence of an acid, the above-mentioned R groups of the functional $-OR$ group can be decomposed into a hydroxyl group in the presence of an acid, and these groups are preferred though the R group may be such that the $-OR$ group is not decomposed in the presence of an acid. The above-mentioned R group may react with resin (A) in the presence of an acid.

The cross-linking agent (C) includes, as preferable examples, compounds represented by formula (2):

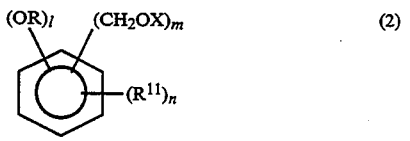

wherein each R is independently selected from the group consisting of a substituted methyl group, a substituted ethyl group, a silyl group, an alkoxycarbonyl group and an acyl group; X is a hydrogen atom, an alkyl group having 1-5 carbon atoms or an R group which is as defined above, and when m is 2 or more X's may be the same as or different from each other; $R^{11}$ is an alkyl group having 1-4 carbon atoms, a phenyl group or a naphthyl group and when n is 2 or more $R^{11}$'s may be the same as or different from each other; and l, m and n are integers of 0 or more and satisfy the following conditions: $1+m+n \leq 6$, $1 \leq l$, and $1 \leq m$, compounds represented by formula (3):

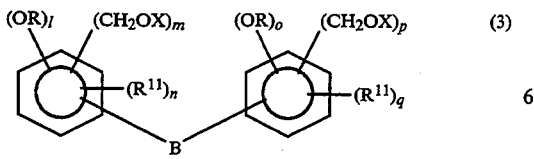

wherein X, R and $R^{11}$ are as defined in formula (2); l, m, n, o, p and q are integers of 0 or more and satisfy the following conditions: $1+m+n \leq 5$, $o+p+q \leq 5$, $1 \leq 1+o$, and $1 \leq m+p$; and B is a single bond, $-S-$, $-O-$,

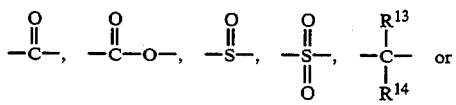

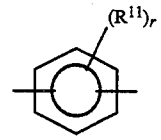

in which $R^{11}$ is as defined in formula (2), $R^{13}$ and $R^{14}$ are independently hydrogen atoms, alkyl groups having 1-6 carbon atoms, acyl groups, phenyl groups or naphthyl groups, and r is an integer satisfying the condition: $0 \leq r < 4$, compounds represented by formula (4):

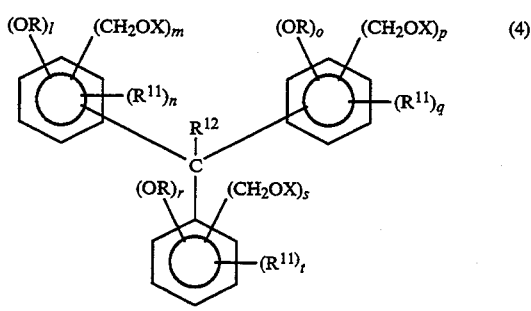

wherein X, R and $R^{11}$ are as defined in formula (2); l, m, n, o, p, q, r, s and t are integers of 0 or more and satisfy the following conditions: $1+m+n \leq 5$, $o+p+q \leq 5$, $r+s+t \leq 5$, $1 \leq 1+o+r$, and $1 \leq m+p+s$; and $R^{12}$ is a hydrogen atom, an alkyl group having 1-4 carbon atoms or a phenyl group, compounds represented by formula (5):

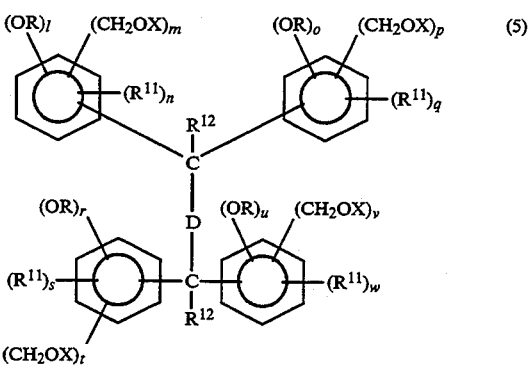

wherein X, R, $R^{11}$ and $R^{12}$ are as defined in formula (4); l, m, n, o, p, q, r, s, t, u, v and w are integers of 0 or more and satisfy the following conditions: $1+m+n \leq 5$, $o+p+q \leq 5$, $r+s+t \leq 5$, $u+v+w \leq 5$, $1 \leq 1+o+r+u$, and $1 \leq m+p+s+v$; D is a single bond, $-S-$, $-O-$,

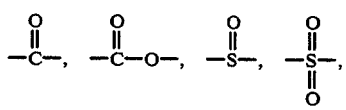

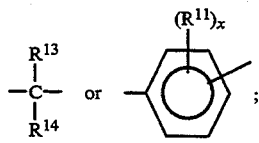

and $R^{11}$, $R^{13}$, $R^{14}$ and X are as defined in formula (2), compounds represented by formula (6):

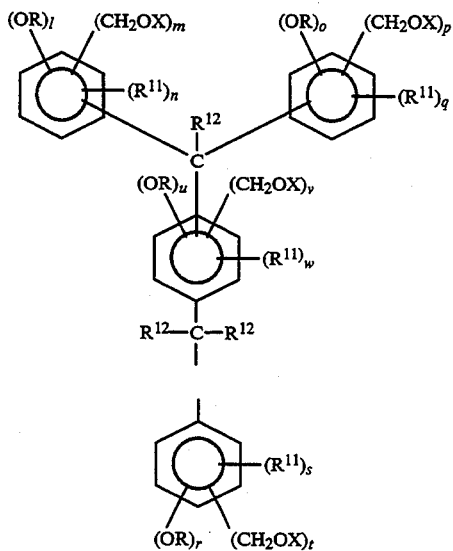

wherein X, R, $R^{11}$ and $R^{12}$ are as defined in formula (4); l, m, n, o, p, q, r, s, t, u, v and w are integers of 0 or more and satisfy the following conditions: $1+m+n \leq 5$, $o+p+q \leq 5$, $r+s+t \leq 5$, $1 \leq l+o+r+u$, $1 \leq m+p+t+v$, and $u+v+w \leq 4$, resins having structural units represented by formula (7):

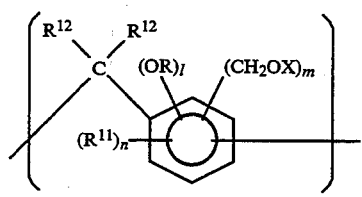

wherein X, R, $R^{11}$ and $R^{12}$ are as defined in formula (4); and l, m and n are integers of 0 or more and satisfy the following conditions: $1+m+n \leq 4$, $1 \leq l$, and $1 \leq m$, and resins having structural units represented by formula (8):

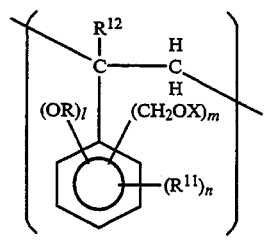

wherein X, R, $R^{11}$ and $R^{12}$ are as defined in formula (4); and l, m and n are integers of 0 or more and satisfy the following conditions: $1+m+n \leq 5$, $1 \leq l$, and $1 \leq m$.

The cross-linking agent (C) can be synthesized by, for example, the following method:

A phenol compound is reacted with formaldehyde (specifically, formaline, trioxane, hemiformal and paraformaldehyde are suitably used) in the presence of a catalyst (specifically, an alkali metal hydroxide, and an alkaline earth metal hydroxide are suitably used) to synthesize a corresponding methylol group-containing phenol compound. Subsequently, an R group is introduced into the phenol compound to convert the phenolic hydroxyl group to a functional OR group. With some kinds of protective groups, an R group is also introduced into the alcoholic hydroxyl group of the methylol group in the above R-group-introducing step. However, even in this case, if R is a group having such properties that the functional OR group per se can be reacted with resin (A) in the presence of an acid or can be hydrolyzed to a methylol group, which can be reacted, such an R group can be used without any problem.

The amount of the cross-linking agent (C) added is preferably 5–70 parts by weight, more preferalby 10–50 parts by weight and most preferably 15–40 parts by weight, per 100 parts by weight of the resin (A).

The resin (A) is not critical as far as it can be dissolved in a developing solution consisting of an aqueous alkaline solution, and preferable examples of the resin (A) are novolak resins and poly(hydroxystyrene) type resins.

The novolak resin is a resin obtained by polymerizing a phenol compound and an aldehyde with an acid catalyst. The phenol compound includes, for example, phenol, o-cresol, m-cresol, p-cresol, o-ethylphenol, m-ethylphenol, p-ethylphenol, o-butylphenol, m-butylphenol, p-butylphenol, 2,3-xylenol, 2,4-xylenol, 2,5-xylenol, 3,4-xylenol, 3,5-xylenol, 2,3,5-trimethylphenol, 3,4,5-trimethylphenol, p-phenylphenol, hydroquinone, catechol, resorcinol, 2-methylresorcinol, 2-methylhydroquinone, phloroglucinol, pyrogallol, 1-naphthol, 2-naphthol, bisphenol A, dihydroxybenzoic acid esters, gallic acid esters and the like.

Of these phenol compounds, particularly preferable are o-cresol, m-cresol, p-cresol, m-ethylphenol, 2,3-xylenol, 2,5-xylenol, 3,4-xylenol, 3,5-xylenol, 2,3,5-trimethylphenol, hydroquinone, resorcinol, 2-methylresorcinol, phloroglucinol, pyrogallol and bisphenol A.

The above phenol compounds may be used alone or in admixture of two or more.

The aldehyde includes, for example, formaldehyde, acetaldehyde, propyl aidehyde, benzaldehyde, phenylacetaldehyde, α-phenylpropyl aidehyde, β-phenylpropyl aidehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, p-nitrobenzaldehyde, o-methylbenzaldehyde, m-methylbenzaldehyde, p-methylbenzaldehyde, p-ethylbenzaldehyde, p-n-butylbenzaldehyde, furfural and the like. In particular, formaldehyde is appropriately used.

The source of generating formaldehyde includes formaline, trioxane, paraformaldehyde, methylhemiformal, ethylhemiformal, propylhemiformal, butylhemiformal, phenylhemiformal and the like. In particular, formaline and butylhemiformal are suitably used.

The above aldehydes may be used alone or in admixture of two or more. The aldehyde is preferably used in an amount of 0.7–3 moles per mole of the phenol compound.

The acid catalyst used in the polycondensation includes hydrochloric acid, nitric acid, sulfuric acid, formic acid, oxalic acid, acetic acid, paratoluenesulfonic acid and the like. The amount of the acid catalyst used is preferably $1 \times 10^{-4}$ to $5 \times 10^{-1}$ mole per mole of the phenol compound.

In the polycondensation, water is preferably used as a solvent; however, when the phenol compound used in the polycondensation is not dissolved in an aqueous aldehyde solution and forms a heterogenous phase at the initial of the reaction, a hydrophilic solvent may be used as a reaction medium. This hydrophilic solvent includes, for example, alcohols such as methanol, ethanol, propanol, butanol and the like; and cyclic ethers such as tetrahydrofuran, dioxane and the like. The amount of the solvent is preferably 20–1,000 parts by weight per 100 parts by weight of the reactants.

The polystyrene-reduced weight average molecular weight (referred to hereinafter as Mw) of the novolak resin used in this invention is preferably 2,000–25,000, more preferably 3,500–15,000. There is a tendency that when Mw is less than 2,000, developability and thermal durability become inferior, and when it exceeds 25,000, developability, sensitivity and resolution become inferior.

The poly(hydroxystyrene) type resin is a polymer having a structural unit corresponding to a structure formed by cleavage of the polymerizable double bond of a hydroxystyrene as shown below (the structural unit is referred to hereinafter as the poly(hydroxystyrene) structural unit).

The hydroxystyrene includes, for example, o-hydroxystyrene, m-hydroxystyrene, p-hydroxystyrene, 3-chloro-4-hydroxystyrene, 4-chloro-3-hydroxystyrene, 4-bromo-3-hydroxystyrene, 3-ethyl-4-hydroxystyrene, 3-propyl-4-hydroxystyrene, 3-t-butyl-4-hydroxystyrene, 3-phenyl-4-hydroxystyrene, 3-naphthyl-4-hydroxystyrene, 3-benzyl-4-hydroxystyrene, styryl-4-hydroxystyrene, 3-vinyl-4-hydroxystyrene, 3-propenyl-4-hydroxystyrene, 3-cumyl-4-hydroxystyrene, 2-methyl-4-hydroxystyrene, 2,6-dimethyl-4-hydroxystyrene, p-hydroxy-α-methylstyrene, m-hydroxy-α-methylstyrene, o-hydroxy-α-methylstyrene and the like.

The above poly(hydroxystyrene) type resins can be produced by polymerization, such as radical polymerization, cationic polymerization, anionic polymerization, thermal polymerization or the like, of a corresponding hydroxystyrene, or alternatively, by protecting the phenolic hydroxyl group of a corresponding hydroxystyrene with a t-butyl group, an acetyl group, a t-butoxycarbonyl group, a trialkylsilyl group or the like, then polymerizing the protected hydroxystyrene and thereafter removing the protecting group by hydrolysis.

The poly(hydroxystyrene) type resin may have, in addition to the above-mentioned structural units, other structural units such as structural units formed by cleavage of the double bond of a monomer such as acrylic acid, methyl acrylate, ethyl acrylate, glycidyl acrylate, propyl acrylate, methyl vinyl ether, t-butyl vinyl ether, styrene, α-methylstyrene, p-methylstyrene, chlorostyrene, maleic anhydride, vinyl acetate, vinylpyridine, vinylpyrrolidone or acrylonitrile (referred to hereinafter as the other structural units). The proportion of the other structural units contained is preferably 50% or less, more preferably 20% or less, of the total of the other structural units and the polyhydroxystyrene structural unit.

The Mw of the poly(hydroxystyrene) type resin used in this invention is preferably 5,000–300,000, more preferably 10,000–150,000. When the Mw is less than 5,000, there is a tendency that sensitivity and thermal durability become inferior, and when it exceeds 300,000, there is a tendency that developability, resolution and coatability become inferior.

The resin (A) can be used in the form of a hydrogenation product having a hydrogenation degree of 70% or less, preferably 50% or less, more preferably 40% or less. When the hydrogenation degree exceeds 70%, the tendency that the solubility in an aqueous alkaline solution is lowered and the pattern-forming ability becomes insufficient is increased. Also, dry-etching resistance becomes inferior and unsatisfactory ethcing tends to be caused.

The acid-generating agent (B) is, for example, an onium salt, a halogen-containing compound, a quinonediazide compound, a sulfone compound, a nitrobenzyl compound or the like, and includes, specifically, the following compounds:

Onium salts: Iodonium salts, sulfonium salts, ammonium salts, etc., preferably compounds represented by formula (9):

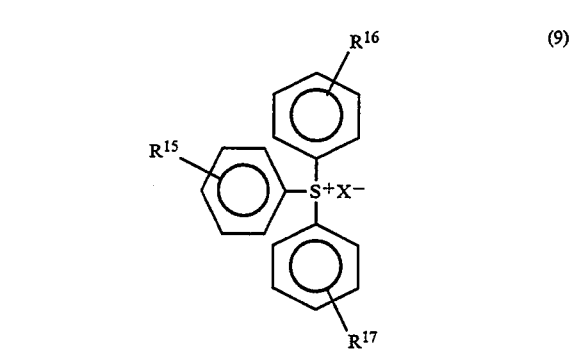

wherein $R^{15}$, $R^{16}$ and $R^{17}$ are the same as or different from each other and each thereof is a hydrogen atom, an amino group, a nitro group, a cyano group, an alkyl group having 1–4 carbon atoms or an alkoxy group having 1–4 carbon atoms, and X is $SbF_6$, $AsF_6$, $PF_6$, $BF_4$, $CF_3CO_2$, $ClO_4$, $CF_3SO_3$,

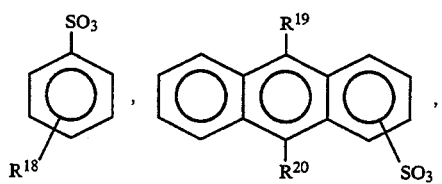

-continued

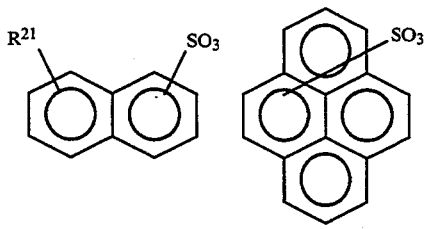

in which $R^{18}$ is a hydrogen atom, an amino group, an anilino group, an alkyl group having 1-4 carbon atoms, an alkoxy group having 1-4 carbon atoms, and each of $R^{19}$ and $R^{20}$ is an alkoxy group having 1-4 carbon atoms, and $R^2$ is a hydrogen atom, an amino group, an anilino group, an alkyl group having 1-4 carbon atoms or an alkoxy group having 1-4 carbon atoms, compounds represented by formula (10):

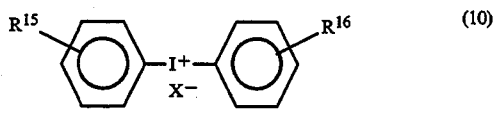
(10)

wherein $R^{15}$, $R^{16}$ and x are as defined in formula (9), and compounds represented by formula (11):

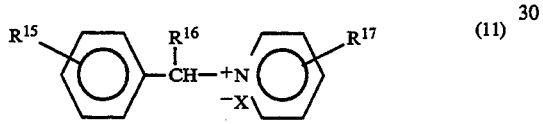
(11)

wherein $R^{15}$, $R^{16}$, $R^{17}$ and X are as defined in formula (9).

Halogen-containing compounds: Haloalkyl-containing hydrocarbon compounds, haloalkyl-containing heterocyclic compounds, etc., preferably compounds represented by formula (12):

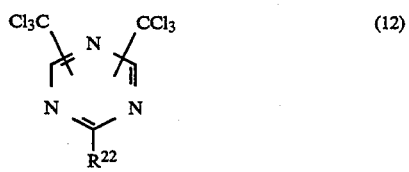
(12)

wherein $R^{22}$ is a trichloromethyl group, a phenyl group, a methoxyphenyl group, a naphthyl group or a methoxynaphthyl group, and compounds represented by formula (13):

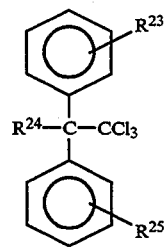
(13)

wherein $R^{23}$, $R^{24}$ and $R^{25}$ are the same as or different from each other and each thereof is a hydrogen atom, a halogen atom, a methyl group, a methoxy group or a hydroxyl group.

Quinonediazide compounds: Diazobenzoquinone compounds, diazonaphthoquinone compounds, etc., preferably compounds represented by formula (14):

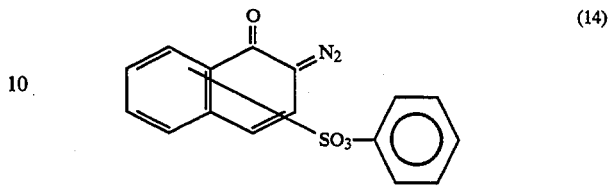
(14)

compounds represented by formula (15):

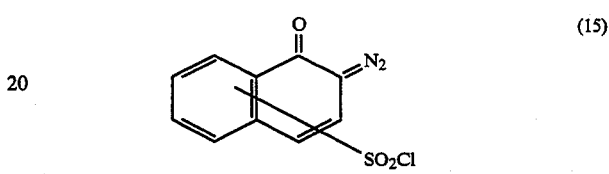
(15)

compounds represented by formula (16):

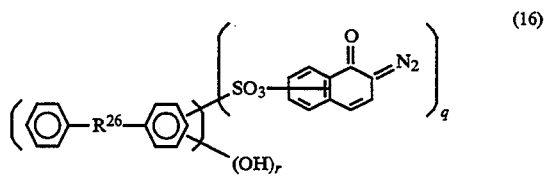
(16)

wherein $R^{26}$ is $-CH_2-$, $-C(CH_3)_2-$,

or $-SO_2-$, q is an integer of 1-6 and r is an integer of 0-5, provided that the total of q and r is 1-6, and compounds represented by formula (17):

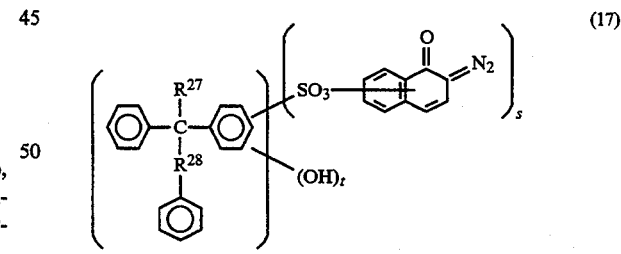
(17)

wherein $R^{27}$ is a hydrogen atom or a methyl group, $R^{28}$ has the same meaning as $R^{26}$ in formula (16), s is an integer of 1-6 and t is an integer of 0-5, provided that the total of s and t is 1-6.

Sulfone compounds: β-Ketosulfones, β-sulfonylsulfones, etc., preferably compounds represented by formula (18):

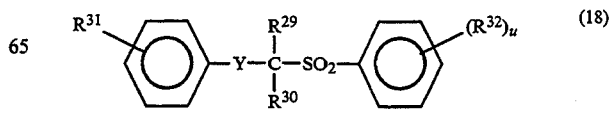
(18)

wherein Y is

or —SO$_2$, R$^{29}$, R$^{30}$, R$^{31}$ and R$^{32}$ are the same as or different from each other and each thereof is an alkyl group having 1–4 carbon atoms or a halogen atom, and n is an integer of 0–3.

Nitrobenzyl compounds: Nitrobenzylsulfonate compounds, dinitrobenzylsulfonate compounds, etc., preferably compounds represented by formula (19):

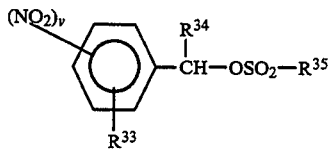

wherein R$^{33}$ is an alkyl group having 1–4 carbon atoms; R$^{34}$ is a hydrogen atom or a methyl group; R$^{35}$ is

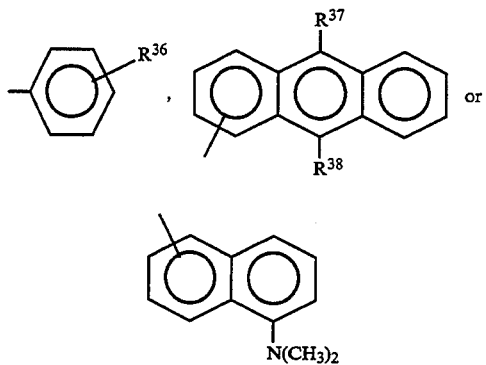

in which R$^{36}$ is a hydrogen atom or a methyl group, R$^{37}$ and R$^{38}$ are the same as or different from each other, and each thereof is an alkoxy group having 1–4 carbon atoms; and n is an integer of 1–3.

Sulfonic acid compounds: Alkylsulfonic acid esters, haloalkylsulfonic acid esters, arylsulfonic acid esters, iminosulfonates, etc., preferably compounds represented by formula (20):

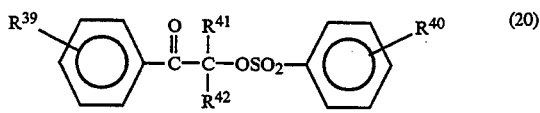

wherein R$^{39}$ and R$^{40}$ are the same as or different from each other and each thereof is a hydrogen atom or an alkyl group having 1–4 carbon atoms and R$^{41}$ and R$^{42}$ are the same as or different from each other and each thereof is a hydrogen atom, an alkyl group having 1–4 carbon atoms or an aryl group having 6–20 carbon atoms, compounds represented by formula (21):

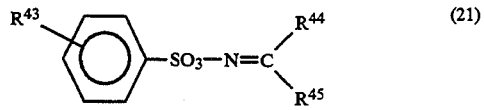

wherein R$^{43}$ is a hydrogen atom or an alkyl group having 1–4 carbon atoms, and R$^{44}$ and R$^{45}$ are the same as or different from each other and each thereof is an alkyl group having 1–4 carbon atoms or an aryl group having 6–20 carbon atoms, provided that R$^{44}$ and R$^{45}$ may be bonded to each other to form a ring together with the nitrogen atom to which they attach, compounds represented by formula (22):

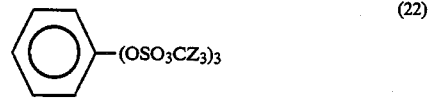

wherein Z is a fluorine atom or a chlorine atom.

Of these compounds, onium salts are particularly preferred.

The amount of the acid-generating agent (B) added is preferably 1–70 parts by weight, more preferably 3–50 parts by weight, and most preferably 3–20 parts by weight, per 100 parts by weight of the resin (A). When the amount is less than 1 part by weight, it is difficult to obtain a sufficient pattern-forming ability, and when it exceeds 70 parts by weight, scum tends to be formed.

The swelling-inhibiting agent (D) has a solubility in an alkali developing solution and possesses an intramolecularly hydrogen-bonded phenolic hydroxyl group in its molecule. Such structural features make low the alkali-solubility of the composition of this invention, and further enables the pattern to be inhibited from being swollen during the development, whereby the resolution is enhanced.

The swelling-inhibiting agent (D) is a phenolic compound represented by formula (1), and the alkyl group in the definitions of R$^1$–R$^{10}$ of formula (1) includes methyl, ethyl, n-propyl, i-propyl, t-butyl and the like, and the alkoxy group in the same definitions includes methoxy, ethoxy, n-propoxy, i-propoxy, t-butoxy and the like.

The swelling-inhibiting agent (D) can be prepared by reacting, under acidic conditions, a phenol compound with a methylolated compound of a bisphenol compound obtained by reacting a bisphenol compound with formaldehyde with an alkaline catalyst.

The bisphenol compound includes preferably bisphenol A [4,4'-(1-methylethylidene)bisphenol], bisphenol F (4,4'-methylenebisphenol), bisphenol E (4,4'-ethylidenebisphenol), bisphenol Z (4,4'-cyclohexylidenebisphenol), bisphenol S (4,4'-sulfonyldiphenol), 4,4'-(1,3-dimethylbutylidene)bisphenol, 4,4'-(1-phenylethylidene)bisphenol, 4,4'-(2-methylpropylidene)bisphenol, 4,4'-oxybisphenol, 4,4'-propanediylbisphenol, 4,4'-(1-methylpropylidene)bisphenol, 4,4'-(3-methylbutylidene)bisphenol and 4,4'(phenylmethylene)bisphenol.

The above-mentioned phenol compound is preferably a monohydric phenol compound, and more preferably a monohydric phenol compound having a substituent or substituents in the 5- and/or 2-positions. The phenol compound includes specifically phenol, p-cresol, p-ethylphenol, p-propylphenol, p-butylphenol, 2,4-xylenol, 2-methyl-4-ethylphenol, 2-methyl-4-butylphenol, 4-butyl-2-methylphenol, p-methoxyphenol, p-ethoxyphenol, p-propoxyphenol, p-butoxyphenol and the like.

Such swelling-inhibiting agents (D) include, for example, the following compounds:
2,2',6,6'-tetrakis(2-hydroxybenzyl)bisphenol A, 2,2',6,6'-tetrakis(2-hydroxy-5-methylbenzyl)bisphenol A,
2,2',6,6'-tetakis(5-t-butyl-2-hydroxybenzyl)bisphenol A,
2,2',6,6'-tetrakis(3,5-dimethyl-2-hydroxybenzyl)bisphenol A,
2,2',6,6'-tetrakis(2-hydroxybenzyl)bisphenol F,
2,2',6,6'-tetrakis(2-hydroxy-5-methylbenzyl)bisphenol F,
2,2',6,6'-tetrakis(5-t-butyl-2-hydroxybenzyl)bisphenol F,
2,2',6,6'-tetrakis(3,5-dimethyl-2-hydroxybenzyl)bisphenol F,
2,2',6,6'-tetrakis(2-hydroxybenzyl)bisphenol S,
2,2',6,6'-tetrakis(2-hydroxy-5-methylbenzyl)bisphenol S,
2,2',6,6'-tetrakis(5-t-butyl-2-hydroxybenzyl)bisphenol S,
2,2',6,6'-tetrakis(3,5-dimethyl-2-hydroxybenzyl)bisphenol S,
2,2',6,6'-tetrakis(2-hydroxybenzyl)bisphenol Z,
2,2',6,6'-tetrakis(2-hydroxy-5-methylbenzyl)bisphenol Z,
2,2',6,6'-tetrakis(5-t-butyl-2-hydroxybenzyl)bisphenol Z,
2,2',6,6'-tetrakis(3,5-dimethylbenzyl)bisphenol Z,
2,2',6,6'-tetrakis(2-hydroxybenzyl)bisphenol E,
2,2',6,6'-tetakis(2-hydroxy-5-methylbenzyl)bisphenol E,
2,2',6,6'-tetrakis(5-t-butyl-2-hydroxybenzyl)bisphenol E,
2,2',6,6'-tetrakis(3,5-dimethyl-2-hydroxybenzyl)bisphenol E,
bis[3,4-bis(2'-hydroxybenzyl)-4-hydroxyphenyl]phenylmethane,
bis[3,5-bis(2'-hydroxy-5'-methylbenzyl)-4-hydroxyphenyl]phenylmethane,
bis[3,5-bis(5'-t-butyl-2'-hydroxybenzyl)-4-hydroxyphenyl]phenylmethane,
bis[3,5-bis(3',5'-dimethyl-2'-hydroxybenzyl)-4-hydroxyphenyl]phenylmethane,
1,1-bis[3,5-bis(2'-hydroxybenzyl)-4-hydroxyphenyl]-1-phenylethane,
1,1-bis[3,5-bis(2'-hydroxy-5'-methylbenzyl)-4-hydroxyphenyl]-1-phenylethane,
bis[3,5-bis(5'-t-butyl-2'-hydroxybenzyl)-4-hydroxyphenyl] -1-phenylethane, and
1,1-bis[3,5-bis(3',5'-dimethyl-2'-hydroxybenzyl)-4-hydroxyphenyl]-1-phenylethane.

Of these compounds, the following compounds are preferred:
2,2',6,6'-tetrakis(2-hydroxy-5-methylbenzyl)bisphenol A,
2,2',6,6'-tetrakis(5-t-butyl-2-hydroxybenzyl)bisphenol A,
2,2',6,6'-tetrakis(3,5-dimethyl-2-hydroxybenzyl)bisphenol A,
2,2',6,6'-tetrakis(2-hydroxy-5-methylbenzyl)bisphenol F,
2,2',6,6'-tetrakis(5-t-butyl-2-hydroxybenzyl)bisphenol F,
2,2',6,6'-tetrakis(3,5-dimethyl-2-hydroxybenzyl)bisphenol F,
2,2',6,6'-tetrakis(2-hydroxy-5-methylbenzyl)bisphenol S,
2,2',6,6'-tetrakis(2-hydroxy-5-methylbenzyl)bisphenol Z,
2,2',6,6'-tetrakis(2-hydroxy-5-methylbenzyl)bisphenol E,
bis[3,5-bis(2'-hydroxy-5'-methylbenzyl)-4-hydroxyphenyl]-1-phenylmethane, and
1,1-bis[3,5-bis(2'-hydroxy-5'-methylbenzyl)-4-hydroxyphenyl]-1-phenylethane.

The amount of the swelling-inhibiting agent (D) added is preferably not more than 50 parts by weight, more preferably 3–30 parts by weight and most preferably 5–20 parts by weight, per 100 parts by weight of the resin (A). When the amount exceeds 50 parts by weight, the developability of the unexposed parts is lowered, whereby the formation of a pattern becomes difficult.

The composition of this invention may have added thereto additives such as sensitizer, surfactant and the like.

Because the sensitizer can enhance the apparent sensitivity of the composition of this invention, it is added for the purpose of absorbing the energy of radiation and transferring the energy to the acid-generating agent, to increase the amount of the acid generated. As such a sensitizer, there may be preferably used, for example, acetone, benzene, acetophenones, naphthalenes, biacetyl, Eosine, Rose Bengal, pyrenes, anthracenes, phenothiazines and the like. The amount of the sensitizer added is preferably not more than 30 parts by weight, more preferably not more than 15 parts by weight, per 100 parts by weight of the resin (A).

The surfactant is added for improving the coatability and developability of a radiation-sensitive resin composition, and such surfactants include, for example, non-ionic surfactants such as polyoxyethylene lauryl ether, polyoxyethylene oleyl ether, polyoxyethylene octylphenyl ether, polyoxyethylene nonylphenyl ether, polyethylene glycol dilaurate, polyethylene glycol distearate, and the like; fluorine-containing surfactants such as F Top EF 301, EF 303 and EF 352 (products of Shin Akita Kase K.K.), Megafac F 171, F 172 and F 173 (products of DAINIPPON INK & CHEMICALS), Fluorad FC 430 and FC 431 (products of Sumitomo 3M Limited), Asahi Guard AG 710, Surflon S-382, Surflon SC-101, SC-102, SC-103, SC-104, SC-105 and SC-106 (products of Asahi Glass Co., Ltd.) and the like; organosiloxane polymer KP 341 (product of Shin-Etsu Chemical Co., Ltd.); and Polyflow No. 75 and No. 95 (products of Kyoeisha Yushikagaku Kogyo K.K.) which are acrylic or methacrylic acid (co)polymers; and so forth. The amount of the surfactant added is preferably not more than 2 parts by weight per 100 parts by weight of the solid content of the composition.

The composition of this invention may further contain a dye or pigment for lowering the influence of halation during the irradiation with a radiation, and also an adhesive for improving the adhesiveness of the composition. If necessary, a storage-stabilizer, a defoaming agent and the like may be incorporated into the composition.

The composition of this invention can be prepared by dissolving the resin (A), the acid-generating agent (B), the cross-linking agent (C) and others optional components including the swelling-inhibiting agent (D) in a solvent so that the solid concentration is, for example, 20–40% by weight, and passing the resulting solution through a filter having a pore diameter of about 0.2 μm.

As the solvent, there may be used, for example, ethylene glycol monomethyl ether, ethylene glycol monoethyl ether, ethylene glycol methyl ether acetate, ethylene glycol ethyl ether acetate, diethylene glycol monomethyl ether, diethylene glycol monoethyl ether, propylene glycol methyl ether acetate, propylene glycol propyl ether acetate, toluene, xylene, methyl ethyl ketone, cyclohexanone, 2-heptanone, 3-heptanone, 4-heptanone, ethyl 2-hydroxypropionate, ethyl 2-hydroxy-2-methylpropinate, ethyl ethoxyacetate, ethyl hydroxyacetate, methyl 2-hydroxy-3-methylbutanoate, methyl 3-methoxypropionate, ethyl 3-methoxypropionate, ethyl acetate, butyl acetate, ethyl pyruvate, and the like.

A high boiling solvent may further be added, which includes N-methytlformamide, N,N-dimethylformamide, N-methylformanilide, N-methylacetamide, N,N-dimethylacetamide, N-methylpyrrolidone, dimethylsulfoxide, benzyl ethyl ether, dihexyl ether, acetonyl acetone, isophorone, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, propylene carbonate, phenyl Cellosolve acetate and the like.

The composition of this invention is coated by spin-coating, flow-coating, roll-coating or the like on a silicon wafer or a wafer coated with aluminum or the like, and then heated to form a negative type resist layer, which is then irradiated with a radiation through a desired mask pattern and then developed with a developing solution, to form a pattern.

When the composition of this invention is used, it is preferable to coat the composition on the wafer or the like, subject the resulting assembly to prebaking and exposure, then heat the same at 70°–140° C., and thereafter subject the same to development.

As the developing solution for the composition of this invention, there may be used an aqueous alkaline solution prepared by dissolving in water an alkaline compound such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, dimethylethanolamine, triethanolamine, tetramethylammonium hydroxide, tetraethylammonium hydroxide, choline, pyrrol, piperidine, 1,8-diazabicyclo(5.4.0)-7-undecene, 1,5-diazabicyclo(4.3.0)-5-nonane or the like so that the concentration is preferably 1–10% by weight, more preferably 2–5% by weight.

To the developing solution may be added appropriate amounts of a water-soluble organic solvent, for example, an alcohol such as methanol, ethanol or the like, and a surfactant.

When the development is conducted with a developing solution consisting of such an aqueous alkaline solution, in general, rinsing with water is subsequently effected.

This invention is explained in more detail below referring to Examples, which are not by way of limitation but by way of illustration.

In the Examples, measurement of Mw and evaluation of resist were conducted according to the following methods.

Mw:

Using a GPC column manufactured by Toso (consisting of two G2000H$_{XL}$ columns, one G3000H$_{XL}$ column and one G4000H$_{XL}$ column), Mw was measured by a gel permeation chromatography using a monodisperse polystyrene as a standard under the analysis conditions that the flow rate was 1.0 ml/min, tetrahydrofuran was used as an eluent and the column temperature was 40° C.

Optimum exposure:

A resist pattern was formed on a wafer by development with a 2.38% by weight aqueous tetramethylammonium hydroxide solution by an immersion method at 23° C. for 1 minute, rinsing with water for 30 seconds and subsequent drying, and an exposure necessary for forming a line and space pattern of 0.6 μm (1L1S) in a 1:1 width (referred to hereafter as the optimum exposure) was determined. The exposure was conducted with a 248 nm KrF laser using MBK-400TL-N manufactured by Admon Science Inc.

Resolution degree:

The dimension of the minimum resist pattern obtained when exposure was effected for the optimum exposure time was measured.

Yield of residual film thickness:

The pattern thickness after development for the optimum exposure time was divided by the resist film thickness before exposure and the quotient obtained was multiplied by 100. The figure obtained is expressed as percent.

Developability:

Scum and undeveloped portion in the unexposed part and swelling of the exposed part and curved line of pattern were checked.

Thermal durability:

A wafer on which a resist pattern had been formed was placed in a clean oven. When the pattern was not broken at 150° C., this sample is indicated "good".

Synthesis Example 1

In 100 ml of dioxane were dissolved 176 g (1.0 mole) of p-t-butoxystyrene and 8.2 g (0.05 mole) of azobisisobutyronitrile, and the resulting solution was subjected to reaction for 24 hours while the internal temperature was kept at 70° C., after which the reaction mixture was subjected to several reprecipitation treatments to remove the unreacted monomer, thereby obtaining poly(p-t-butoxystyrene). Subsequently, this poly(p-t-butoxystyrene) was hydrolyzed with an acid to obtain poly(p-hydroxystyrene) having a Mw of 30,000. This resin is referred to hereafter as Resin A1.

Synthesis Example 2

In 100 ml of dioxane were dissolved 176 g (1.0 mole) of p-t-butoxystyrene, 4.0 g (0.02 mole) of dodecylmercaptan and 8.2 g (0.05 mole) of azobisisobutyronitrile, and the resulting solution was subjected to reaction for 10 hours while the internal temperature was kept at 75° C., after which the reaction mixture was subjected to several reprecipitation treatments to remove the unreacted monomer, thereby obtaining poly(p-t-butoxystyrene). Subsequently, this poly(p-t-butoxystyrene) was hydrolyzed with an acid to obtain poly(p-hydroxystyrene) having a Mw of 8,900. This resin is referred to hereinafter as Resin A2.

Synthesis Example 3

To an aqueous mixed solution formed by dissolving, in 200 ml of water, 108 g (1.0 mole) of p-cresol and 44 g (1.1 moles) of sodium hydroxide was added 37% by weight formaline (2.2 moles of formaldehyde) while the temperature was kept at 10° C. or lower. The temperature of the resulting mixture was gradually elevated to room temperature while the mixture was stirred, after which the mixture was subjected to reaction for 3 days. Subsequently, a 10% by weight aqueous hydrochloric acid solution was slowly added to the reaction mixture while the mixture was cooled so that the temperature was not elevated by heat of neutralization, to neutralize the mixture. The solids precipitated were separated by filtration and then washed with cold water several times until the washings became neutral. The solids were vacuum-dried to obtain 2,6-dihydroxymethyl-4-methylphenol (referred to hereinafter as DMP).

Synthesis Example 4

To a solution prepared by dissolving 16.8 g (0.1 mole) of DMP obtained in Synthesis Example 3 in 200 ml of 1,4-dioxane was gradually added 322 g (2.0 moles) of hexamethyldisilazane (referred to hereinafter as HMDS). The resulting solution was then subjected to reaction under reflux for 2 hours, and the reaction mixture was concentrated under reduced pressure to remove the excessive HMDS, dioxane, ammonia and the like, thereby obtaining a brown, oily silylated DMP. This was purified by distillation under reduced pressure (1.5 mmHg, 127°–131° C.), to obtain a compound represented by the following structural formula, and this compound is referred to hereafter as Cross-linking Agent C1:

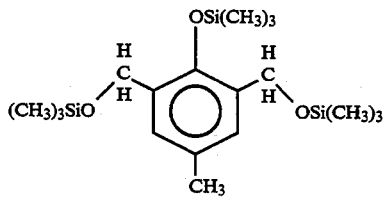

Synthesis Example 5

In 200 ml of 1,4-dioxane were dissolved 16.8 g (0.1 mole) of DMP obtained in Synthesis Example 3, 42.1 g (0.5 mole) of 3,4-dihydro-2H-pyrane and 0.86 g ($5 \times 10^{-3}$ mole) of paratoluenesulfonic acid, and the resulting solution was subjected to reaction for 8 hours while the internal temperature was kept at 10° C. or lower, after which 100 ml of a 10% by weight aqueous sodium hydroxide solution was added to the reaciton mixture. The organic substances were extracted with ethyl acetate and then washed with water several times until the washings became neutral. Subsequently, the organic layer was concentrated under reduced pressure to obtain a compound represented by the following formula, and this compound is referred to hereinafter as Cross-linking Agent C2:

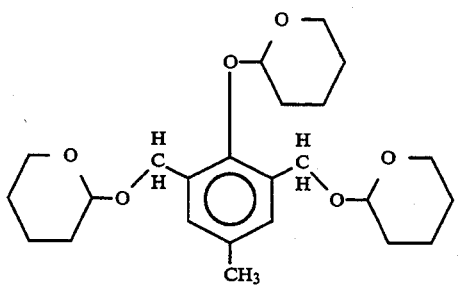

Synthesis Example 6

In 100 ml of water were dissolved 16.8 g (0.1 mole) of DMP obtained in Synthesis Example 3 and 4.4 g (0.11 mole) of sodium hydroxide. To the resulting solution were added 322 mg ($10^{-3}$ mole) of tetra-n-butylammonium bromide and 10.5 g (0.09 mole) of benzyl chloride, and the resulting mixture was stirred at room temperature for 2 days. Subsequently, the organic substance of the reaction mixture was extracted with ethyl acetate, and washed with water several times until the washings became neutral. Subsequently, the organic layer was concentrated under reduced pressure to obtain a brown, oily product, which was then recrystallized from ethyl acetate and hexane to obtain a compound represented by the following formula, and this compound is referred to hereinafter as Cross-linking Agent C3:

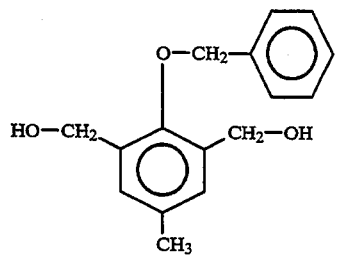

Synthesis Example 7

To 42.0 g (0.25 mole) of DMP obtained in Synthesis Example 3 was added a solution prepared by dissolving 11 g (0.275 mole) of sodium hydroxide in 50 ml of water. Subsequently, 17.5 g (0.1 mole) of $\alpha,\alpha'$-dichloroorthoxylene and 300 ml of methanol were added thereto, and the resulting mixture was subjected to reaction under reflux for 8 hours. Subsequently, the reaction mixture was poured into 1 liter of water to separate a white precipitate, which was then collected by filtration, washed with water and toluene, and then dried to obtain a compound represented by the following structural formula, and this compound is referred to hereinafter as Cross-linking Agent C4:

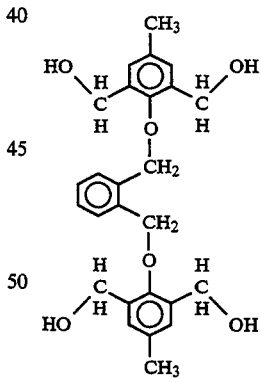

Synthesis Example 8

In 50 ml of dimethylsulfoxide were dissolved 4.62 g (0.01 mole) of Cross-linking Agent C4 obtained in Synthesis Example 7, 6.74 g (0.08 mole) of 3,4-dihydro-2H-pyrane and 503 mg ($2 \times 10^{-4}$ mole) of pyridinium paratoluenesulfonate, and the resulting solution was subjected to reaction at 50° C. for 6 hours, after which 50 ml of a 1% by weight aqueous sodium carbonate solution was added thereto. The resulting mixture was subjected to extraction with ethyl acetate, and the extract was washed with water to obtain an oily compound represented by the following structural formula, and this compound is referred to hereinafter as Cross-linking Agent C5:

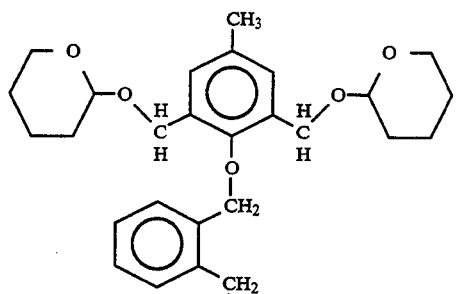

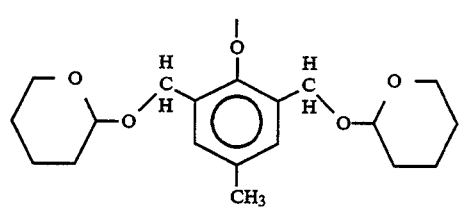

Synthesis Example 9

In dried dioxane was suspended 4.62 g (0.01 mole) of Cross-linking Agent C4 obtained in Synthesis Example 7, and 2.4 g of sodium hydride having a purity of 60% by weight (corresponding to 0.06 mole of sodium hydride) was further added to the suspension with stirring. The stirring was continuated for a further 1 hour. Subsequently, the resulting precipitate was separated, washed with dried toluene several times under a nitrogen atmosphere. Subsequently, 10.0 g (0.0705 mole) of methyl iodide was added to the precipitate, and the resulting mixture was stirred for 2 hours. After completion of the reaciton, the dioxane and the excessive methyl iodide were removed by distillation under reduced pressure, after which the residue was extracted with ethyl acetate. The organic layer was washed with water and then the ethyl acetate was removed again by distillation under reduced pressure, to obtain a compound represented by the following structural formula, and this compound is referred to hereinafter as Cross-linking Agent C6:

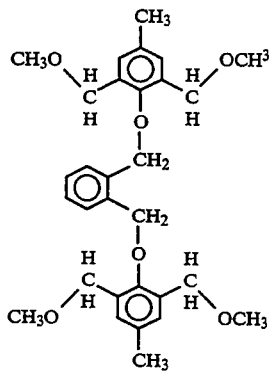

Synthesis Example 10

To reaction were subjected 22.8 g (0.1 mole) of bisphenol A, 8.8 g (0.22 mole) of sodium hydroxide and 35.7 g (0.44 mole in terms of formaldehyde) of 37% by weight aqueous formaline solution at 40° C. for 4 hours.

After completion of the reaction, the reaciton mixture was neutralized with acetic acid while the mixture was cooled with ice so that the internal temperature did not exceed 20° C., upon which a product was precipitated. Subsequently, the product was extracted with 50 ml of ethylene glycol monoethyl ether acetate and the organic layer was washed with water. Thereafter, 108 g (1 mole) of p-cresol and 1.9 g of paratoluenesulfonic acid monohydrate were added to the organic layer, and the resulting mixture was subjected to reaciton under reflux for 2 hours, from which the solvent, unreacted paracresol and the like were removed, upon which a brown resin was obtained. This resin was dissolved in toluene and the undissolved precipitate was collected by filtration, and then washed with toluene to obtain 2,2',6,6'-tetrakis(2-hydroxy-5-methylbenzyl)bisphenol A, the swelling-inhibiting agent, represented by the following structural formula, and this compound is referred to hereinafter as Swelling-Inhibiting Agent D1:

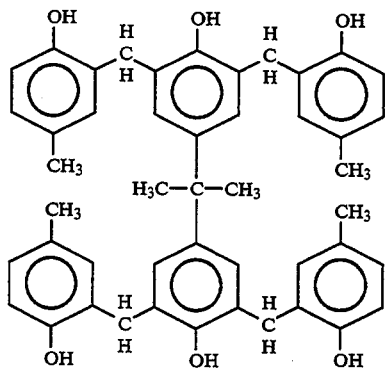

Synthesis Example 11

In the same manner as in Synthesis Example 10, 22.8 g (0.1 mole) of bisphenol A, 8.8 g (0.22 mole) of sodium hydroxide and 35.7 g (0.44 mole in terms of formaldehyde) of 35% by weight aqueous formaline solution were subjected to reaction, and the reaction mixture was then after-treated. Thereafter, the reaction mixture was subjected to reaction with 122 g (1.0 mole) of 2,4-xylenol and then after-treated, to obtain 2,2',6,6'-tetrakis(3,5-dimethyl-2-hydroxybenzyl)bisphenol A represented by the following structural formula, and this compound is referred to hereinafter as Swelling-Inhibiting Agent D2:

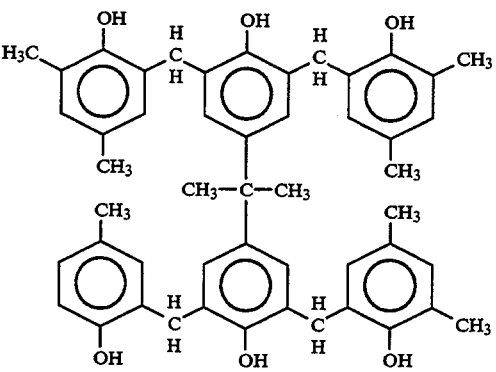

Examples 1–8 and Comparative Examples 1–2

The resin (A), acid-generating agent (B), cross-linking agent (C), swelling-inhibiting agent (D) and solvent shown in Table 1 were mixed in the proportions shown in Table 2 (parts are by weight) to form uniform solutions, and the solutions were filtered through a membrane filter having a pore diameter of 0.2 μm to obtain composition solutions.

Each of the composition solutions was coated on a silicon wafer by a spinner, and then pre-baked at 100° C. for 100 seconds to form a resist film having a thickness of 1.0 μm.

A pattern was intimately contacted with the resist film and exposed to a KrF laser, and then subjected to baking after exposure at 110° C. for 90 seconds. Subsequently, the baked film was subjected to development and then rinsed. The results of evaluation of the resist are shown in the following Table.

Table

| | Resin | | Acid-generating agent | | Cross-linking agent | | Swelling-inhibiting agent | | Solvent | | Optimum exposure (mJ/cm$^2$) | Resolution degree (μm) | Yield of residual film thickness (%) | Developability | Heat resistance |
|---|---|---|---|---|---|---|---|---|---|---|---|---|---|---|---|
| | Kind | A-mount (part) | Kind | A-mount (part) | Kind | A-mount (part) | Kind | A-mount (part) | Kind | A-mount (part) | | | | | |
| Ex. 1 | A1 | 100 | B1 | 3 | C1 | 25 | — | — | γ | 370 | 10 | 0.30 | 98 | Good | Good |
| 2 | A1 | 100 | B2 | 3 | C3 | 30 | — | — | β | 399 | 50 | 0.35 | 96 | Good | Good |
| 3 | A1 | 100 | B3 | 4 | C4 | 25 | — | — | δ | 387 | 30 | 0.35 | 95 | Good | Good |
| 4 | A1 | 100 | B1 | 3 | C5 | 25 | — | — | β | 366 | 50 | 0.30 | 97 | Good | Good |
| 5 | A2 | 100 | B1 | 2 | C6 | 35 | D1 | 20 | γ | 520 | 20 | 0.28 | 97 | Good | Good |
| 6 | A2 | 100 | B1 | 2 | C5 | 30 | D1 | 15 | α | 450 | 25 | 0.28 | 98 | Good | Good |
| 7 | A2 | 100 | B1 | 2 | C2 | 35 | D2 | 10 | β | 450 | 25 | 0.28 | 97 | Good | Good |
| 8 | A2 | 100 | B1 | 2 | C2 | 40 | D1 | 15 | β | 481 | 20 | 0.28 | 97 | Good | Good |
| Comp. Ex. 1 | A1 | 100 | B1 | 3 | DMP | 25 | — | — | γ | 370 | —[1] | 0.65 | 96 | Bad[2] | — |
| 2 | A1 | 100 | B2 | 3 | C7 | 30 | — | — | β | 399 | —[1] | 0.65 | 95 | Bad[3] | — |

Note:
[1]: No pattern of 0.60 μm was formed and the optimum exposure could not be measured.
[2]: Swelling of pattern and presence of scum were observed.
[3]: Swelling of pattern was observed.
B1: Triphenylsulfonium trifluoromethanesulfonate
B2: Triphenylsulfonium hexafluoroantimonate
B3: Diphenyliodonium tetrafluoroborate
α: Ethylene glycol monoethyl ether acetate
β: Methyl 3-methxoypropionate
γ: Ethyl 2-hydroxyproipionate
δ: Ethyl pyruvate
C7: Hexamethoxymethylmelamine

What is claimed is:

1. A negative type radiation-sensitive resin composition comprising:
   (A) an alkali-soluble resin,
   (B) a compound which generates an acid upon irradiation, and
   (C) an aromatic compound having, as functional groups, an —OR group and a —CH$_2$OX group, both bonded directly to the aromatic ring in which R represents a substituted methyl group, a substituted ethyl group, a silyl group, an alkoxycarbonyl group or an acyl group and in which X represents a hydrogen atom, an alkyl group having 1–5 carbon atoms or an R group which is as defined above, and being capable of cross-linking the above alkali-soluble resin in the presence of an acid,
   wherein said substituted methyl group is selected from the group consisting of methoxymethyl, methylthiomethyl, methoxyethoxymethyl, tetrahydropyranyl, tetrahydrofuryl, tetrahydrothiopyranyl, benzyloxymethyl, phenacyl, bromophenacyl, methoxyphenacyl, α-methylphenacyl, bromobenzyl, chlorobenzyl, dichlorobenzyl, nitrobenzyl, methoxybenzyl, iperonyl and allyl,
   and wherein said substituted ethyl group is selected from the group consisting of 1-methoxyethyl and 1-ethoxyethyl.

2. A negative type radiation-sensitive resin composition as claimed in claim 1, wherein R represents a silyl group, an alkoxy carbonyl group or an acyl group.

3. A negative type radiation-sensitive resin composition comprising:
   (A) an alkali-soluble resin,
   (B) a compound which generates an acid upon irradiation,
   (C) an aromatic compound having, as functional groups, an —OR group and a —CH$_2$OX group, both bonded directly to the aromatic ring in which R represents a substituted methyl group, a substituted ethyl group, a silyl group, an alkoxycarbonyl group or an acyl group and in which X represents a hydrogen atom, an alkyl group having 1–5 carbon atoms or an R group which is as defined above, and being capable of cross-linking the above alkali-soluble resin in the presence of an acid, and
   (D) a phenolic compound represented by formula (1):

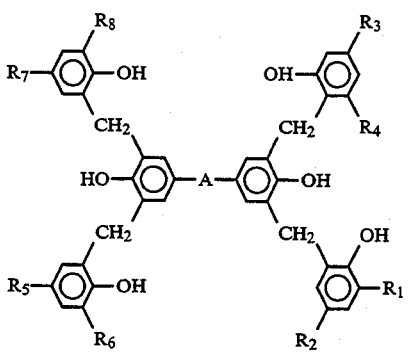

wherein each if R¹-R⁸ represents a substituent selected from the group consisting of hydrogen, alkyl groups having 1–4 carbon atoms and alkoxy groups having 1–4 carbon atoms; A represents a single bond, —S—, —SO₂—, $$-O-, \quad -\overset{\overset{O}{\|}}{C}- \quad \text{or} \quad -\overset{\overset{R^9}{|}}{\underset{\underset{R^{10}}{|}}{C}}-$$

in which each of R⁹ and R¹⁰ represents a substituent selected from the group consisting of hydrogen, alkyl groups having 1–4 carbon atoms, phenyl group and hydroxyphenyl group, provided that when both R⁹ and R¹⁰ are alkyl groups having 1–4 carbon atoms, they may be bonded through a single bond to each other.

4. The negative type radiation-sensitive resin composition according to claim 3, wherein the substituted methyl group in the definition of R is selected from the group consisting of methoxymethyl, methylthiomethyl, methoxyethoxymethyl, tetrahydropyranyl, tetrahydrofuryl, tetrahydrothiopyranyl, benzyloxymethyl, phenacyl, bromophenacyl, methoxyphenacyl, α-methylphenacyl, cyclopropylmethyl, cyclopentyl, cyclohexyl, benzyl, ortho-methylbenzyl, meta-methylbenzyl, paramethylbenzyl, triphenylmethyl, diphenylmethyl, bromobenzyl, nitrobenzyl, methoxybenzyl, piperonyl and allyl.

5. The negative type radiation-sensitive resin composition according to claim 3, wherein the substituted ethyl group in the definition of R is selected from the group consisting of 1-methoxyethyl, 1-ethoxyethyl, isopropyl, t-butyl and 1,1-dimethylpropyl.

6. The negative type radiation-sensitive resin composition according to claim 3, wherein the phenolic compound (D) is selected from the group consisting of:
2,2',6,6,-tetrakis(2-hydroxy-5-methylbenzyl)bisphenol A,
2,2',6,6,-tetrakis(5-t-butyl-2-hydroxybenzyl)bisphenol A,
2,2',6,6'-tetrakis(3,5-dimethyl-2-hydroxybenzyl)bisphenol A,
2,2',6,6'-tetrakis(2-hydroxy-5-methylbenzyl)bisphenol F,
2,2',6,6'-tetrakis(5-t-butyl-2-hydroxybenzyl)bisphenol F,
2,2',6,6'-tetrakis(3,5-dimethyl-2-hydroxybenzyl)bisphenol F,
2,2',6,6'-tetrakis(2-hydroxy-5-methylbenzyl)bisphenol S,
2,2',6,6'-tetrakis(2-hydroxy-5-methylbenzyl)bisphenol Z,
2,2',6,6'-tetrakis(2-hydroxy-5-methylbenzyl)bisphenol E,
bis[3,5-bis(2'-hydroxy-5'-methylbenzyl)-4-hydroxyphenyl-1-phenylmethane, and
1,1-bis[3,5-bis(2'-hydroxy-5'-methylbenzyl)-4-hydroxyphenyl]-1-phenylethane.

7. The negative type radiation-sensitive resin composition according to claim 3, wherein the amount of the phenolic compound (D) is not more than 50 parts by weight per 100 parts by weight of the component (A).

8. The negative type radiation-sensitive resin composition according to claim 7, wherein the amount of the phenolic compound (D) is 5–20 parts by weight.

9. The negative type radiation-sensitive resin composition according to claim 1 or 3, wherein the silyl group in the definition of R is selected from the group consisting of trimethylsilyl, triethylsilyl, t-butyldimethylsilyl, isopropyldimethylsilyl and phenyldimethylsilyl.

10. The negative type radiation-sensitive resin composition according to claim 1 or 3, wherein the alkoxycarbonyl group in the definition of R is selected from the group consisting of methoxycarbonyl, ethoxycarbonyl and t-butoxycarbonyl.

11. The negative type radiation-sensitive resin composition according to claim 1 or 3, wherein the acyl group in the definition of R is selected from the group consisting of acetyl, propionyl, butyryl, heptanoyl, hexanoyl, valeryl, pivaloyl, isovaleryl, lauroyl, myristoyl, palmitoyl, stearoyl, acryloyl, propioloyl, methacryloyl, crotonoyl, oleoyl, furoyl, thenoyl, nicotinoyl, isonicotinoyl, p-toluenesulfonyl and mesyl.

12. The negative type radiation-sensitive resin composition according to claim 1 or 3, wherein R is tetrahydropyranyl, tetrahydrofuryl, benzyl, o-methylbenzyl, m-methylbenzyl, p-methylbenzyl, triphenylmethyl, diphenylmethyl, nitrobenzyl, methoxybenzyl, piperonyl, allyl, 1-methoxyethyl, t-butyl, trimethylsilyl, methoxycarbonyl, ethoxycarbonyl, t-butoxycarbonyl, acetyl or p-toluenesulfonyl.

13. The negative type radiation-sensitive resin composition according to claim 1 or 3, wherein the alkyl group in the definition of X is selected from the group consisting of methyl, ethyl, n-propyl, isopropyl, n-butyl isobutyl, sec-butyl, t-butyl and n-pentyl.

14. The negative type radiation-sensitive resin composition according to claim 1 or 3, wherein the aromatic compound is selected from the group consisting of compounds represented by formulas (2)–(8):

$$\underset{(R^{11})_n}{\underset{|}{\bigcirc}} \quad \overset{(OR)_l \quad (CH_2OX)_m}{} \quad (2)$$

wherein each R is independently selected from the group consisting of a substituted methyl group, a substituted ethyl group, a silyl group, an alkoxycarbonyl group and an acyl group; X is a hydrogen atom, an alkyl group having 1–5 carbon atoms or an R group which is as defined above, and when a plurality of X's are present they may be the same as or different from each other; R¹¹ is an alkyl group having 1–4 carbon atoms, a phenyl group or a naphthyl group and when a plurality of R11's are present they may the same as or different from each other; and l, m and n are integers of 0 or more and satisfy the following conditions: $1+m+n \leq 6$, $1 \leq l$, and $1 \leq m$, $$\underset{(R^{11})_n}{\bigcirc}\overset{(OR)_l \quad (CH_2OX)_m}{}\underset{B}{}\underset{(R^{11})_q}{\bigcirc}\overset{(OR)_o \quad (CH_2OX)_p}{} \quad (3)$$

wherein X, R and R¹¹ are as defined in formula (2); l, m, n, o, p and q are integers of 0 or more and satisfy the following conditions: $1+m+n \leq 5$, $o+p+q \leq 5$, $1 \leq l+o$, and $1 \leq m+p$; and B is a single bond, —S—, —O—,

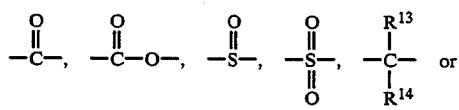

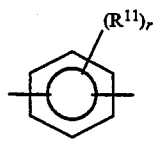

in which $R^{11}$ is as defined in formula (2), $R^{13}$ and $R^{14}$ are independently hydrogen atoms, alkyl groups having 1–6 carbon atoms, acyl groups, phenyl groups or naphthyl groups, and r is an integer satisfying the condition: $0 \leq r \leq 4$,

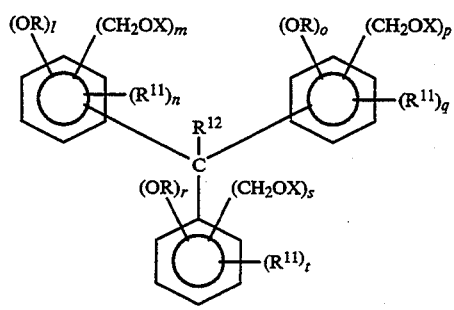

(4)

wherein X, R and $R^{11}$ are as defined in formula (2); l, m, n, o, p, q, r, s and t are integers of 0 or more and satisfy the following conditions: $l+m+n \leq 5$, $o+p+q \leq 5$, $r+s+t \leq 5$, $1 \leq l+o+r$, and $1 \leq m+p+s$; and $R^{12}$ is a hydrogen atom, an alkyl group having 1–4 carbon atoms or a phenyl group,

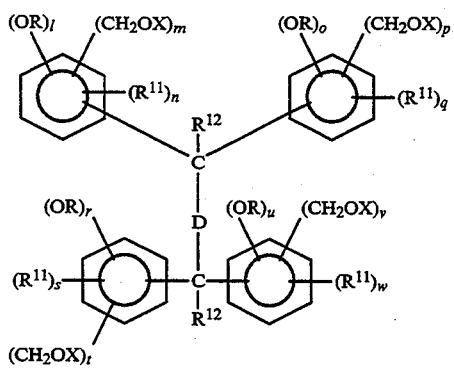

(5)

wherein X, R, $R^{11}$ and $R^{12}$ are as defined in formula (4); l, m, n, o, p, q, r, s, t, u, v and w are integers of 0 or more and satisfy the following conditions: $l+m+n \leq 5$, $o+p+q \leq 5$, $r+s+t \leq 5$, $u+v+w \leq 5$, $o+r+u$, and $1 \leq m+p+s+v$; D is a single bond,

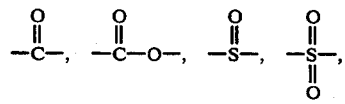

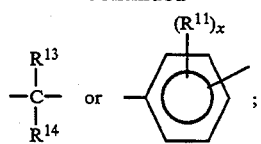

and $R^{11}$, $R^{13}$, $R^{14}$ and X are as defined in formula (2),

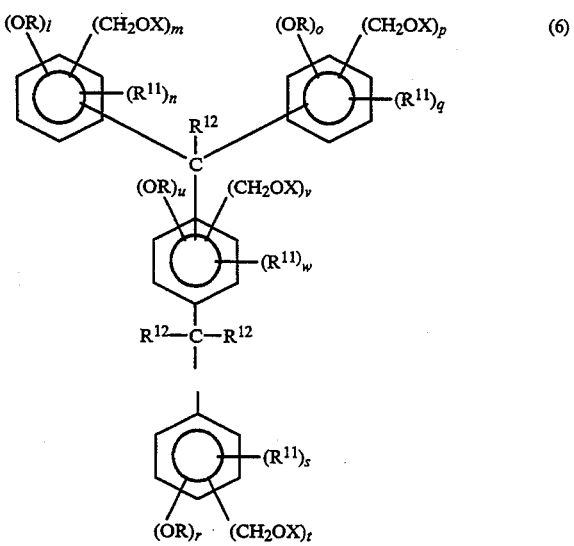

(6)

wherein X, R, $R^{11}$ and $R^{12}$ are as defined in formula (4); l, m, n, o, p, q, r, s, t, u, v and w are integers of 0 or more and satisfy the following conditions: $l+m+n \leq 5$, $o+p+q \leq 5$, $r+s+t \leq 5$, $1 \leq l+o+r+u$, $1 \leq m+p+t+v$, and $u+v+w \leq 4$,

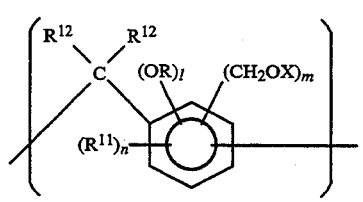

(7)

wherein X, R, $R^{11}$ and $R^{12}$ are as defined in formula (4); and l, m and n are integers of 0 or more and satisfy the following conditions: $l+m+n \leq 4$, $1 \leq l$, and $1 \leq m$, and

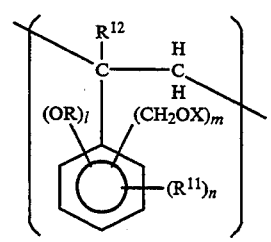

(8)

wherein X, R, $R^{11}$ and $R^{12}$ are as defined in formula (4); and l, m and n are integers of 0 or more and satisfy the following conditions: $l+m+n \leq 5$, $1 \leq l$, and $1 \leq m$.

15. A negative type radiation-sensitive resin composition as claimed in claim 10, wherein the aromatic compound is selected from the group consisting of compounds represented by formulas (3)–(7).

16. The negative type radiation-sensitive resin composition according to claim 1 or 3, wherein the alkali-soluble resin is a novolak resin or a poly(hydroxystyrene) type resin.

17. The negative type radiation-sensitive resin composition according to claim 16, wherein the alkali-soluble resin is in the form of a hydrogenation product having a hydrogenation degree of 70% or less.

18. The negative type radiation-sensitive resin composition according to claim 1 or 3, wherein the compound which generates an acid upon irradiation with a radiation is a sulfonic acid compound, an onium salt, a halogen-containing compound, a quinonediazide compound, a sulfone compound or a nitrobenzyl compound.

19. The negative type radiation-sensitive resin composition according to claim 18, wherein the compound which generates an acid upon irradation is an onium salt.

20. The negative type radiation-sensitive resin composition according to claim 19, wherein the onium salt is an iodonium salt, a sulfonium salt or an ammonium salt.

21. The negative type radiation-sensitive resin composition according to claim 18, wherein the halogen-containing compound is a haloalkyl-containing hydrocarbon compound or a haloalkyl-containing heterocyclic compound.

22. The negative type radiation-sensitive resin composition according to claim 18, wherein the quinonediazide compound is a diazobenzoquinone compound or a diazonaphthoquinone compound.

23. The negative type radiation-sensitive resin composition according to claim 18, wherein the sulfone compound is a $\beta$-ketosulfone or a $\beta$-sulfonylsulfone.

24. The negative type radiation-sensitive resin composition according to claim 18, wherein the nitrobenzyl compound is a nitrobenzylsulfonate compound or a dinitrobenzylsulfonate compound.

25. The negative type radiation-sensitive resin composition according to claim 18, wherein the sulfonic acid compound is an alkylsulfonic acid ester, a haloalkylsulfonic acid ester, an arylsulfonic acid ester or an iminosulfonate.

26. The negative type radiation-sensitive resin composition according to claim 1 or 3, wherein the amount of the component (B) is 1–70 parts by weight per 100 parts by weight of the component (A) and the amount of the component (C) is 5–70 parts by weight per 100 parts by weight of the component (A).

27. The negative type radiation-sensitive resin composition according to claim 26, wherein the amount of the component (B) is 3–20 parts by weight and the amount of the component (C) is 15–40 parts by weight.

* * * * *